(12) United States Patent
Nozawa et al.

(10) Patent No.: US 11,369,265 B2
(45) Date of Patent: Jun. 28, 2022

(54) OPHTHALMIC APPARATUS

(71) Applicant: Tomey Corporation, Nagoya (JP)

(72) Inventors: Yuji Nozawa, Nagoya (JP); Masahiro Yamanari, Nagoya (JP); Takashi Kamo, Nagoya (JP)

(73) Assignee: TOMEY CORPORATION, Nagoya (JP)

( * ) Notice: Subject to any disclaimer, the term of this patent is extended or adjusted under 35 U.S.C. 154(b) by 421 days.

(21) Appl. No.: 16/703,487

(22) Filed: Dec. 4, 2019

(65) Prior Publication Data
US 2020/0178791 A1 Jun. 11, 2020

(30) Foreign Application Priority Data

Dec. 5, 2018 (JP) .............................. JP2018-228126

(51) Int. Cl.
G01B 9/02 (2022.01)
A61B 3/10 (2006.01)
(Continued)

(52) U.S. Cl.
CPC ............ *A61B 3/102* (2013.01); *A61B 5/0066* (2013.01); *G01B 9/02004* (2013.01);
(Continued)

(58) Field of Classification Search
CPC .. A61B 3/102; A61B 5/0066; G01B 9/02004; G01B 9/02007; G01B 9/02027;
(Continued)

(56) References Cited

U.S. PATENT DOCUMENTS 5,994,690 A * 11/1999 Kulkarni ............ G01B 9/02091
250/363.04
9,192,294 B2 11/2015 Sharma et al.
(Continued)

FOREIGN PATENT DOCUMENTS

EP 2949264 A1 12/2015
JP 2008122295 A 5/2008
(Continued)

Primary Examiner — Tarifur R Chowdhury
Assistant Examiner — Jonathon Cook
(74) Attorney, Agent, or Firm — Shumaker, Loop & Kendrick, LLP

(57) ABSTRACT

An ophthalmic apparatus may include: a wavelength sweeping light source; a reference optical system; a calibration optical system; a light receiving element configured to receive calibration interference light which is a combination of calibration light and reference light; and a signal processor configured to sample a calibration interference signal outputted from the light receiving element when it receives the calibration interference light. The signal processor may sample the calibration interference light in at least first and second frequency bands, which are different and used for measuring a specific region of a subject eye. The ophthalmic apparatus calculates a difference between first and second waveforms, the first waveform being a waveform of the calibration interference signal that is sampled in the first frequency band and Fourier transformed, the second waveform being a waveform of the calibration interference signal that is sampled in the second frequency band and Fourier transformed.

7 Claims, 10 Drawing Sheets

(51) Int. Cl.
*A61B 5/00* (2006.01)
*G01B 9/02004* (2022.01)
*G01B 9/02001* (2022.01)
*G01B 9/02055* (2022.01)
*G01B 9/02091* (2022.01)

(52) U.S. Cl.
CPC ..... *G01B 9/02007* (2013.01); *G01B 9/02074* (2013.01); *G01B 9/02083* (2013.01); *G01B 9/02091* (2013.01)

(58) Field of Classification Search
CPC .............. G01B 9/0207; G01B 9/02072; G01B 9/02074; G01B 9/02075; G01B 9/02083; G01B 9/02091; G01B 2290/60
See application file for complete search history.

(56) References Cited

U.S. PATENT DOCUMENTS

| | | | |
|---|---|---|---|
| 2008/0285043 A1* | 11/2008 | Fercher | G01B 9/02019 356/451 |
| 2008/0297806 A1* | 12/2008 | Motaghiannezam | G01B 9/02004 356/484 |
| 2009/0261240 A1 | 10/2009 | Watanabe et al. | |
| 2013/0222813 A1 | 8/2013 | Watanabe et al. | |
| 2013/0229627 A1 | 9/2013 | Kato et al. | |
| 2014/0221827 A1* | 8/2014 | Motaghiannezam | A61B 5/1128 356/479 |
| 2014/0327918 A1 | 11/2014 | Sugiyama et al. | |
| 2014/0343411 A1* | 11/2014 | O'Brien | A61B 5/0066 600/425 |
| 2015/0057958 A1 | 2/2015 | Watanabe et al. | |
| 2016/0106319 A1* | 4/2016 | Yasuno | A61B 5/0066 600/425 |

FOREIGN PATENT DOCUMENTS

| | | |
|---|---|---|
| JP | 2010-014459 A | 1/2010 |
| JP | 2013167643 A | 8/2013 |
| JP | 2015226608 A | 12/2015 |
| JP | 2016-041218 A | 3/2016 |
| JP | 2016080411 A | 5/2016 |
| JP | 5946654 B2 | 7/2016 |
| JP | 6198448 B2 | 9/2017 |

* cited by examiner

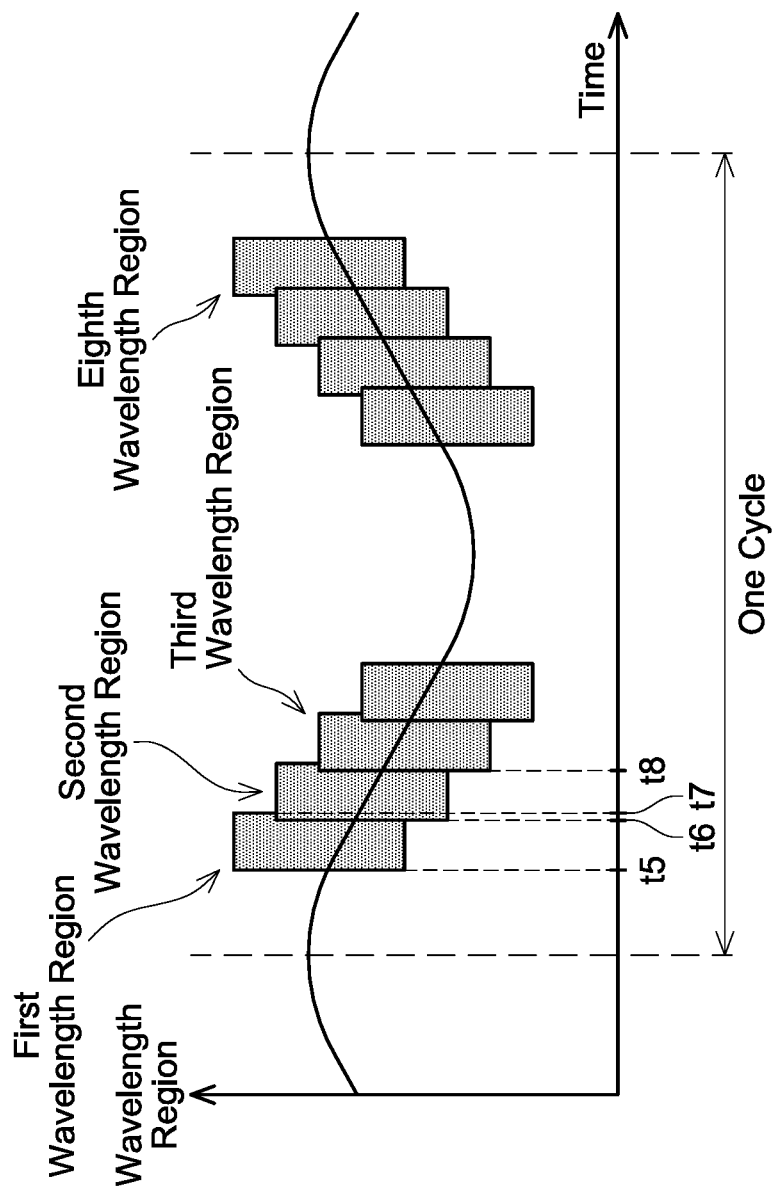

OPHTHALMIC APPARATUS

CROSS-REFERENCE

This application claims priority to Japanese Patent Application No. 2018-228126, filed on Dec. 5, 2018, the entire contents of which are incorporated herein by reference.

TECHNICAL FIELD

The technique disclosed herein relates to an ophthalmic apparatus. To be more precise, it relates to an ophthalmic apparatus configured to measure a subject eye by using optical interferometry.

BACKGROUND ART

Ophthalmic apparatuses configured to capture tomographic images of inside of a subject eye have been developed. For example, an ophthalmic apparatus of Japanese Patent Application Publication No. 2016-41218 is provided with a measurement optical system configured to irradiate a subject eye with light outputted from a light source and guide reflected light from the subject eye, and a reference optical system configured to irradiate a reference surface with the light outputted from the light source and guide reflected light from the reference surface. In measurement, a tomographic image of the subject eye is generated from interference light which is a combination of the reflected light (measurement light) guided by the measurement optical system and the reflected light (reference light) guided by the reference optical system.

SUMMARY

In measurement of a subject eye using an ophthalmic apparatus as described in Japanese Patent Application Publication No. 2016-41218, tomographic information (so-called A-scan information) that indicates a relationship between a position in a depth direction along a measurement optical axis and a signal intensity is acquired from interference light. For example, in a case of acquiring a tomographic image of the subject eye, plural pieces of A-scan information are acquired by scanning measurement light, and a tomographic image of the subject eye is generated by using these plural pieces of A-scan information. Alternatively, also in a case of acquiring A-scan information plural times at the same position in order to improve measurement accuracy, plural pieces of A-scan information are acquired while the same position is irradiated with the measurement light. In order to acquire plural pieces of A-scan information, an interference signal needs to be sampled plural times. Meanwhile, a light source of wavelength sweeping type used in such an ophthalmic apparatus is configured to cyclically sweep a wavelength of light outputted therefrom, and a frequency of the light cyclically changes accordingly. Generally speaking, the A-scan information are desirably acquired at high speed in order to shorten measurement time. For example, the measurement time of the subject eye can be shortened by increasing a speed to sweep the wavelength of the light outputted from the light source, however, this is technically difficult and may result in increased cost. In view of this, considerations are given to acquiring plural pieces of A-scan information in different frequency bands each time the frequency of the light outputted from the light source changes over one cycle. However, sampling (acquiring) interference signals in different frequency bands may cause positional differences and signal intensity differences between the interference signals, since wavelengths (frequency bands) differ between the sampled interference signals. If, for example, a tomographic image is generated using such interference signals, distortion and/or contrast inconsistency may occur in the image. The disclosure herein discloses a technique that suppresses distortion of interference signals caused upon sampling of the interference signals in different frequency bands.

An ophthalmic apparatus disclosed herein may be configured to measure a subject eye by using an optical interferometry. The ophthalmic apparatus may comprise: a light source of wavelength sweeping type; a reference optical system configured to guide light from the light source so as to acquire reference light from the light from the light source; a calibration optical system configured to guide the light from the light source so as to acquire calibration light from the light from the light source; a light receiving element configured to receive calibration interference light, the calibration interference light being a combination of the calibration light and the reference light; a signal processor configured to sample a calibration interference signal, the calibration interference signal being outputted from the light receiving element when the light receiving element receives the calibration interference light; a processor; and a memory storing computer-readable instructions therein. A frequency of the light from the light source may changes cyclically. The signal processor is configured to sample the calibration interference signal in at least a first frequency band and a second frequency band within an entire frequency band that corresponds to one cycle of change in the frequency of the light from the light source, the second frequency band being different from the first frequency band, the first frequency band being used for measuring a specific region of the subject eye, and the second frequency band being used for measuring the specific region of the subject eye. The computer-readable instructions, when executed by the processor, cause the ophthalmic apparatus to calculate a difference between a first waveform and a second waveform, the first waveform being a waveform of the calibration interference signal that is sampled in the first frequency band and Fourier transformed, the second waveform being a waveform of the calibration interference signal that is sampled in the second frequency band and Fourier transformed.

BRIEF DESCRIPTION OF DRAWINGS

FIG. 5A shows a relation between irradiation positions of measurement light and time as well as a relation between the wavelength and time in the ophthalmic apparatus according to the present embodiment, FIG. 5B shows a relation between time and the irradiation positions of the measurement light during a time period from time t1 to time t2 of FIG. 5A, and FIG. 5C shows a relation between time and irradiation positions of measurement light during a time period from time t1 to time t2 in an ophthalmic apparatus of a comparative example.

FIG. 8 is a diagram for explaining timings to sample the interference signals plural times while the wavelength of the light outputted from the light source changes over one cycle (in a case where wavelength regions in which the interference signals are sampled are partially overlapped).

FIG. 9A is a schematic diagram of a tomographic image generated by using A-scan information free from positional differences and signal intensity differences between interference signals, and FIG. 9B is a schematic diagram of a tomographic image generated by using A-scan information with positional differences between interference signals.

DETAILED DESCRIPTION

Figure 1:
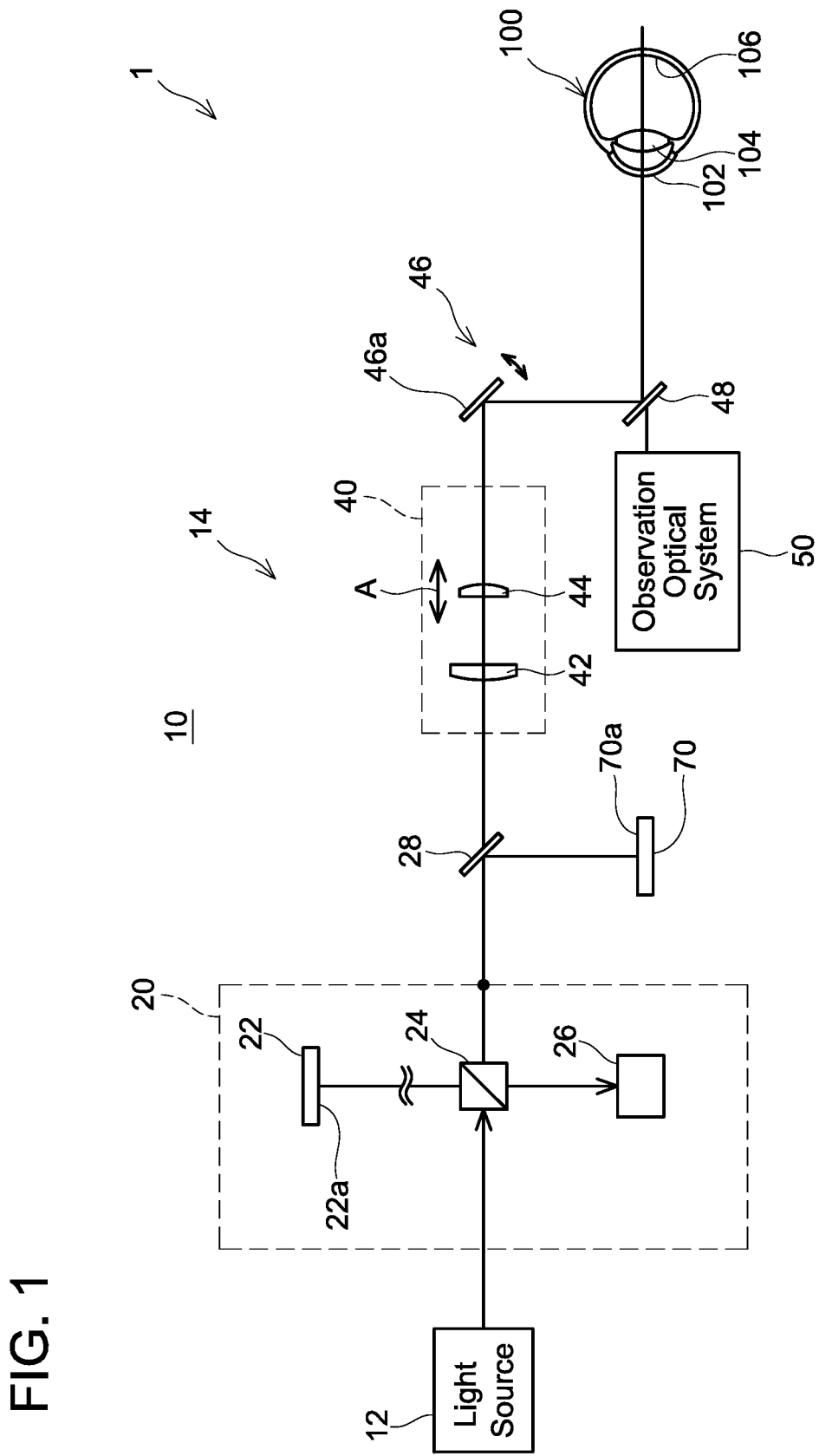
FIG. 1 shows a schematic configuration of an optical system of an ophthalmic apparatus according to a first embodiment.

Representative, non-limiting examples of the present disclosure will now be described in further detail with reference to the attached drawings. This detailed description is merely intended to teach a person of skill in the art further details for practicing preferred aspects of the present teachings and is not intended to limit the scope of the present disclosure. Furthermore, each of the additional features and teachings disclosed below may be utilized separately or in conjunction with other features and teachings to provide improved ophthalmic apparatuses, as well as methods for using and manufacturing the same.

Moreover, combinations of features and steps disclosed in the following detailed description may not be necessary to practice the present disclosure in the broadest sense, and are instead taught merely to particularly describe representative examples of the present disclosure. Furthermore, various features of the above-described and below-described representative examples, as well as the various independent and dependent claims, may be combined in ways that are not specifically and explicitly enumerated in order to provide additional useful embodiments of the present teachings.

All features disclosed in the description and/or the claims are intended to be disclosed separately and independently from each other for the purpose of original written disclosure, as well as for the purpose of restricting the claimed subject matter, independent of the compositions of the features in the embodiments and/or the claims. In addition, all value ranges or indications of groups of entities are intended to disclose every possible intermediate value or intermediate entity for the purpose of original written disclosure, as well as for the purpose of restricting the claimed subject matter.

Some of the features characteristic to below-described embodiments will herein be listed. It should be noted that the respective technical elements are independent of one another, and are useful solely or in combinations. The combinations thereof are not limited to those described in the claims as originally filed.

An ophthalmic apparatus disclosed herein may be configured to measure a subject eye by using an optical interferometry. The ophthalmic apparatus may comprise: a light source of wavelength sweeping type; a reference optical system configured to guide light from the light source so as to acquire reference light from the light from the light source; a calibration optical system configured to guide the light from the light source so as to acquire calibration light from the light from the light source; a light receiving element configured to receive calibration interference light, the calibration interference light being a combination of the calibration light and the reference light; a signal processor configured to sample a calibration interference signal, the calibration interference signal being outputted from the light receiving element when the light receiving element receives the calibration interference light; a processor; and a memory storing computer-readable instructions therein. A frequency of the light from the light source may change cyclically. The signal processor may be configured to sample the calibration interference signal in at least a first frequency band and a second frequency band within an entire frequency band that corresponds to one cycle of change in the frequency of the light from the light source, the second frequency band being different from the first frequency band, the first frequency band being used for measuring a specific region of the subject eye, and the second frequency band being used for measuring the specific region of the subject eye. The computer-readable instructions, when executed by the processor, may cause the ophthalmic apparatus to calculate a difference between a first waveform and a second waveform, the first waveform being a waveform of the calibration interference signal that is sampled in the first frequency band and Fourier transformed, the second waveform being a waveform of the calibration interference signal that is sampled in the second frequency band and Fourier transformed.

In the above ophthalmic apparatus, even when the interference signal is sampled plural times in different frequency bands, the difference between the waveforms of the interference signal can be calculated by using the calibration interference signal which is acquired from the calibration light guided by the same calibration optical system. That is, since the first waveform of the calibration interference signal that is sampled in the first frequency band and the second waveform of the calibration interference signal that is sampled in the second frequency band both indicate the same target (calibration light), they are supposed to be detected at the same position with the same waveform shape. Due to this, a difference between the interference signals (calibration interference signals) sampled in the different frequency bands can be detected by calculating the difference between the first and second waveforms. By correcting the interference signals based on the detected difference, distortion in the interference signals upon measurement of the subject eye can be suppressed.

In the ophthalmic apparatus disclosed herein, the computer-readable instructions, when executed by the processor, may cause the ophthalmic apparatus to calculate a difference between a position of the first waveform and a position of the second waveform in a depth direction. According to this configuration, a positional difference in the depth direction between the interference signals sampled in the different frequency bands can suitably be corrected by correcting the interference signals based on the calculated positional difference in the depth direction.

In the ophthalmic apparatus disclosed herein, the computer-readable instructions, when executed by the processor, may cause the ophthalmic apparatus to calculate a difference between a shape of the first waveform and a shape of the second waveform. According to this configuration, a signal intensity difference between the interference signals sampled in the different frequency bands can suitably be corrected by correcting the interference signals based on the calculated shape difference between the waveforms.

The ophthalmic apparatus disclosed herein may further comprise a measurement optical system configured to irradiate the subject eye with the light from the light source and to guide reflected light from the subject eye. The calibration optical system may comprise a calibration member comprising a reflection surface configured to reflect the light from the light source. The calibration member may be detachably disposed on an optical path of the measurement optical system. When the calibration member is not disposed on the optical path of the measurement optical system, the optical path of the measurement optical system may be capable of having the subject eye disposed thereon. According to this configuration, the calibration member is detachably disposed on the optical path of the measurement optical system. For example, in acquiring the calibration interference signal, the calibration member can be disposed at substantially the same position as a position where the subject eye is to be located during measurement. A configuration of the ophthalmic apparatus can be simplified by not disposing the calibration member inside the ophthalmic apparatus.

The ophthalmic apparatus disclosed herein may further comprise a measurement optical system configured to irradiate the subject eye with the light from the light source and to guide reflected light from the subject eye. The calibration optical system may comprise a calibration member comprising a reflection surface configured to reflect the light from the light source. At least a part of an optical path of the calibration optical system may be configured not to overlap with an optical path of the measurement optical system. The calibration member may not be disposed on the optical path of the measurement optical system and may be disposed on the optical path of the calibration optical system. According to this configuration, the calibration member is disposed on the optical path of the calibration optical system but is not disposed on the optical path of the measurement optical system, thus the reflected light from the subject eye (measurement light) and reflected light from the reflection surface of the calibration member (calibration light) can be generated simultaneously. Due to this, a difference between the interference signals can be corrected upon the measurement of the subject eye.

The ophthalmic apparatus disclosed herein may further comprise a measurement optical system configured to irradiate the subject eye with the light from the light source and to guide reflected light from the subject eye. An optical path of the calibration optical system may be configured to overlap with a part of an optical path of the measurement optical system. The calibration light may be generated from reflected light from a reflection surface of an optical member which the measurement optical system comprises. According to this configuration, the calibration light can be generated without an optical member (calibration member) that generates calibration light. Due to this, the calibration light can be generated without increase in the number of components, and further the measurement light and the calibration light can simultaneously be generated upon the measurement of the subject eye.

The ophthalmic apparatus disclosed herein may further comprise a measurement optical system configured to irradiate the subject eye with the light from the light source and to guide reflected light from the subject eye. The light receiving element may be further configured to receive measurement interference light, the measurement interference light being a combination of the reflected light from the subject eye and the reference light. The signal processor may be further configured to sample a measurement interference signal, the measurement interference signal being outputted from the light receiving element when the light receiving element receives the measurement interference light. The computer-readable instructions, when executed by the processor, may cause the ophthalmic apparatus to correct, based on the calculated difference, at least one of the measurement interference signal that is sampled and the measurement interference signal that is sampled and Fourier transformed. According to this configuration, distortion in the interference signals in measuring the subject eye can suitably be suppressed by correcting the measurement interference signal based on the calculated difference.

EMBODIMENTS

First Embodiment

Hereinbelow, an ophthalmic apparatus 1 according to the present embodiment will be described. As shown in FIG. 1, the ophthalmic apparatus 1 includes a measurement unit 10 configured to examine a subject eye 100. The measurement unit 10 includes an interference optical system 14 configured to cause reflected light reflected from the subject eye 100 and reference light to interfere with each other, an observation optical system 50 configured to observe an anterior part of the subject eye 100, an alignment optical system (not shown) configured to align the measurement unit 10 in a predetermined positional relationship with the subject eye 100, and a K-clock generator 80 (shown in FIG. 2) configured to generate K-clock signals. Since an alignment optical system used in a known ophthalmic apparatus may be used as the alignment optical system, a detailed description thereof will be omitted.

The interference optical system 14 is configured of a light source 12, a measurement optical system, a reference optical system, a calibration optical system, and a light receiving element 26. The measurement optical system is an optical system configured to irradiate inside of the subject eye 100 with light from the light source 12 and guide reflected light (measurement light) therefrom. The reference optical system is an optical system configured to irradiate a reference surface 22a with light from the light source 12 and guide reflected light (reference light) therefrom. The calibration optical system is an optical system configured to irradiate a reflection surface 70a with light from the light source 12 and guide reflected light therefrom. The light receiving element 26 receives measurement interference light which is a combination of the reflected light guided by the measurement optical system and the reference light guided by the reference optical system, and calibration interference light which is a combination of the reflected light guided by the calibration optical system and the reference light guided by the reference optical system.

The light source 12 is a wavelength-sweeping light source, and is configured to change a wavelength of the light emitted therefrom at a predetermined cycle. When the wavelength of the light emitted from the light source 12 changes, a reflected position of reflected light that is to interfere with the reference light, among reflected light from respective parts of the subject eye 100 in a depth direction, changes in the depth direction of the subject eye 100 in accordance with the wavelength of the emitted light. Due to this, it is possible to specify positions of the respective parts (such as a crystalline lens 104 and a retina 106) inside the subject eye 100 by measuring the interference light while changing the wavelength of the emitted light.

The measurement optical system is configured of a beam splitter 24, a beam splitter 28, a focal point adjustment mechanism 40, a Galvano scanner 46, and a hot mirror 48. Light emitted from the light source 12 enters the subject eye 100 through the beam splitter 24, the beam splitter 28, the focal point adjustment mechanism 40, the Galvano scanner 46, and the hot mirror 48. Reflected light from the subject eye 100 is guided to the light receiving element 26 through the hot mirror 48, the Galvano scanner 46, the focal point adjustment mechanism 40, the beam splitter 28, and the beam splitter 24.

The focal point adjustment mechanism 40 is provided with a convex lens 42 disposed on a light source 12 side, a convex lens 44 disposed on a subject eye 100 side, and a second driver 56 (shown in FIG. 2) configured to move the convex lens 44 back and forth with respect to the convex lens 42 in an optical axis direction. The convex lens 42 and the convex lens 44 are disposed on an optical axis and are configured to change a position of a focal point of incident parallel light from the light source 12. When the second driver 56 drives the convex lens 44 in directions of arrow A in FIG. 1, the position of the focal point of the light entering the subject eye 100 changes in the depth direction of the subject eye 100, thus the position of the focal point of the light entering the subject eye 100 is adjusted.

The Galvano scanner 46 includes a Galvano mirror 46a and third driver 58 (shown in FIG. 2) configured to tilt the Galvano mirror 46a. An irradiation position of the measurement light to the subject eye 100 is scanned by the third driver 58 tilting the Galvano mirror 46a.

The reference optical system is configured of the beam splitter 24 and a reference mirror 22. A part of light emitted from the light source 12 is reflected by the beam splitter 24, is directed to the reference surface 22a of the reference mirror 22, and then is reflected by the reference surface 22a of the reference mirror 22. Light reflected by the reference mirror 22 is guided to the light receiving element 26 through the beam splitter 24. The reference mirror 22, the beam splitter 24, and the light receiving element 26 are disposed in an interferometer 20, and their positions are fixed. Therefore, in the ophthalmic apparatus 1 of the present embodiment, a reference optical path length of the reference optical system is constant and does not change.

The calibration optical system is configured of the beam splitter 24, the beam splitter 28, and a mirror 70. Light emitted from the light source 12 is reflected by the beam splitter 28 through the beam splitter 24, is directed to the reflection surface 70a of the mirror 70, and is reflected by the reflection surface 70a of the mirror 70. Light reflected by the mirror 70 is guided to the light receiving element 26 through the beam splitters 28 and 24. In the ophthalmic apparatus 1 of the present embodiment, a position of the mirror 70 is fixed. Therefore, an optical path length of the light guided by the calibration optical system (may be referred to as calibration light) is constant and does not change. The mirror 70 is an example of a "calibration member".

Figure 3:
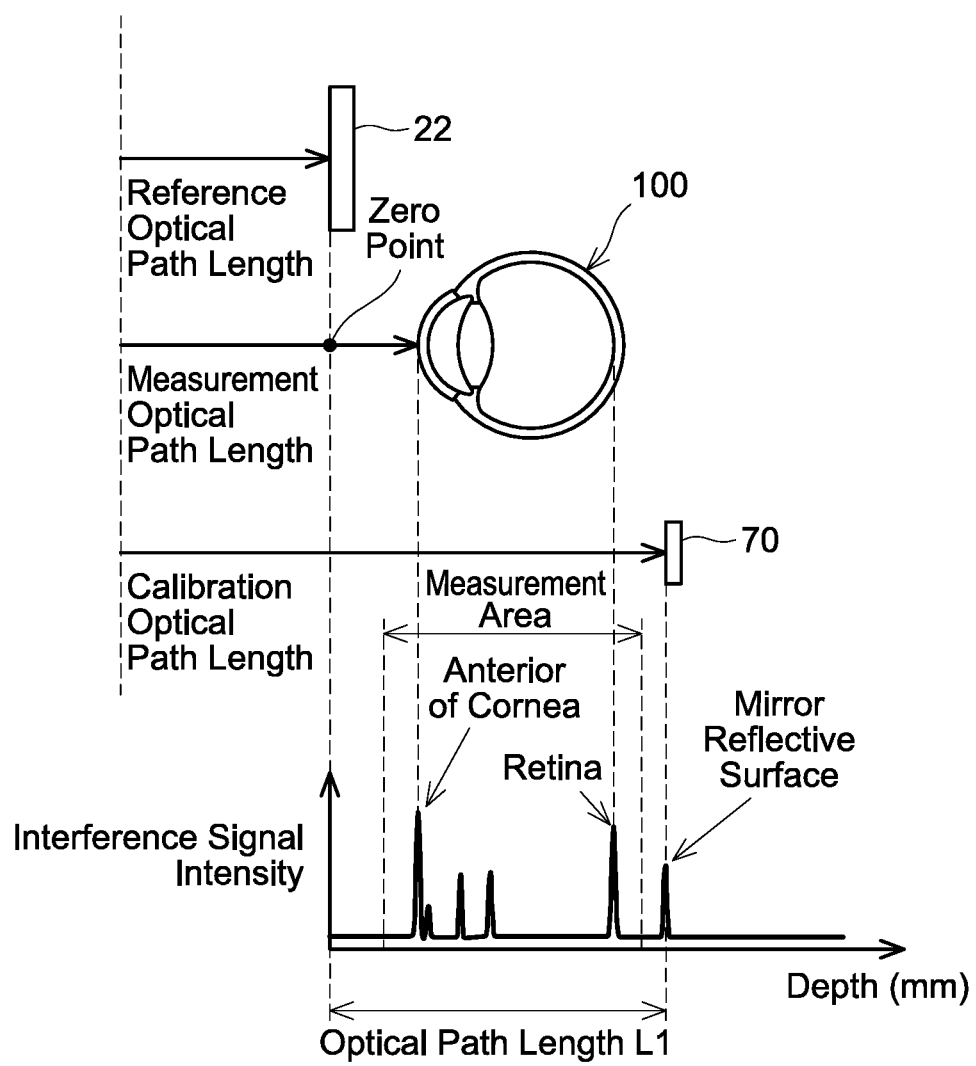
FIG. 3 shows diagrams for explaining a relation between a zero point, a reference optical path length, a measurement optical path length, and a calibration optical path length.

Further, as shown in FIG. 3, in the calibration optical system, the position of the mirror 70 is set with a zero point as a reference thereof and is set such that an optical path length L1 from the zero point to the position of the mirror 70 becomes longer than a distance from the zero point to the retina 106 of the subject eye 100 when the zero point is set at a position on the light source 12 side than the subject eye 100. The zero point herein means a point at which the optical path length of the reference optical system (reference optical path length) coincides with an optical path length of the measurement optical system (measurement optical path length). In the present embodiment, the position of the zero point is set at a predetermined position (for example, a position subtly displaced to the light source 12 side from an anterior surface of a cornea 102). By setting the optical path length L1 of the calibration optical system from the zero point to be longer than the distance from the zero point to the retina 106 of the subject eye 100, the reflection surface 70a of the mirror 70 can be detected without overlapping a measurement area of the subject eye 100 (area from the anterior surface of the cornea 102 to the retina 106). Due to this, a position of the reflection surface 70a can be easily specified.

The light receiving element 26 is configured to detect the measurement interference light which is the combination of the light guided by the reference optical system and the light guided by the measurement optical system and the calibration interference light which is the combination of the light guided by the reference optical system and the light guided by the calibration optical system. The light receiving element 26 is configured to output interference signals according to the measurement interference light and the calibration interference light when the light receiving element 26 receives the measurement interference light and the calibration interference light. That is, the light receiving element 26 outputs a signal generated from the measurement interference light (measurement interference signal) and a signal generated from the calibration interference light (calibration interference signal). These signals are inputted to a processor 64 via a sampling circuit 66 (shown in FIG. 2). A photodiode can be implemented, for example, as the light receiving element 26.

The K-clock generator 80 (shown in FIG. 2) is configured to optically generate sample clock (K-clock) signals from the light from the light source 12 in order to sample the interference signals at a regular frequency interval (at interval regularly set relative to change in a frequency of light). Further, the generated K-clock signals are outputted toward the sampling circuit 66. Due to this, the sampling circuit 66 samples the interference signals based on the K-clock signals, thus the interference signals are sampled at the regular frequency interval.

The interference signals and the K-clock signals are inputted to the sampling circuit 66 (shown in FIG. 2), and the interference signals are sampled at timings defined by the K-clock signals. A known data acquisition apparatus (so-called DAQ) may be used as the sampling circuit 66. The sampling circuit 66 is configured to sample the interference signals plural times to acquire A-scan information regarding inside of the subject eye 100 plural times (which is information indicating a relationship between a depthwise position of an internal structure of the subject eye 100 along a measurement optical axis and a signal intensity). That is, the interference signals acquired by one sampling configure one piece of A-scan information (that is, A-scan information on one scan line, may simply be termed "A-scan information" hereinbelow). As such, plural pieces of A-scan information are acquired by the sampling circuit 66 performing the sampling plural times.

Figure 4:
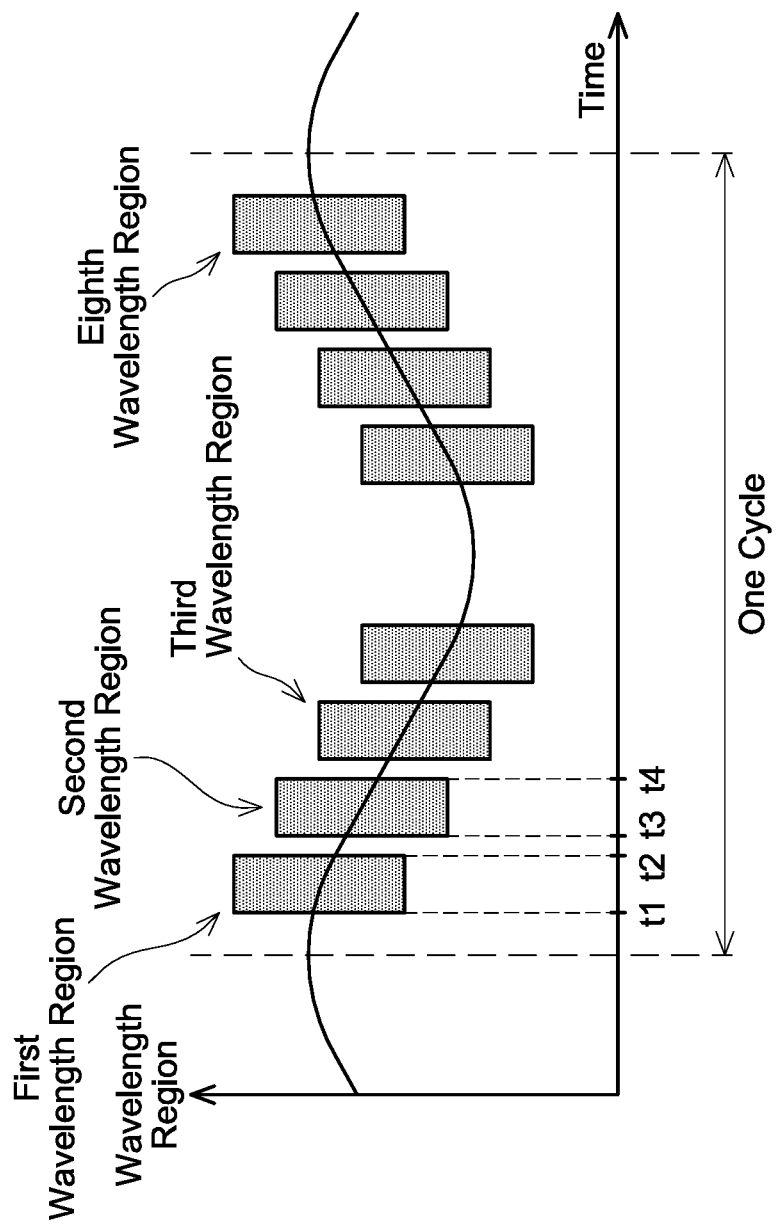
FIG. 4 is a diagram for explaining timings to sample interference signals plural times while a wavelength of light outputted from a light source changes over one cycle (in a case where wavelength regions in which the interference signals are sampled are independent from each other).

Further, as described above, the light source 12 is the wavelength-sweeping light source, therefore a wavelength of the light emitted from the light source 12 is swept cyclically and a frequency of the light also changes cyclically accordingly. Sampling the interference signals once every time the frequency of the light emitted from the light source 12 changes over one cycle (that is, acquiring one piece of A-scan information every cycle) lengthens time required to conduct the measurement plural times. In the present embodiment, the sampling circuit 66 is configured to sample the interference signals plural times in different frequency bands each time the frequency of the light emitted from the light source 12 changes over one cycle. This suppresses time required to conduct the measurement plural times from becoming lengthy. For example, as shown in FIG. 4, when the interference signals are sampled eight times while the wavelength of the light emitted from the light source 12 changes over one cycle (that is, while the frequency changes over one cycle), the time required for the measurements can be significantly shortened, as compared to a case where the interference signals are sampled eight times in the same frequency band. The sampling circuit 66 is an example of a "signal processor".

In the following description, a time period from when the wavelength of the light emitted from the light source 12 becomes the largest until when the wavelength becomes the largest again is termed one cycle (that is, one cycle of the frequency), a wavelength region in which the interference signals are sampled first within the one cycle (which is a wavelength region from time t1 to t2 in FIG. 4) is termed a first wavelength region, and a wavelength region in which the interference signals are sampled immediately after the first wavelength region (which is a wavelength region from time t3 to t4 in FIG. 4) is termed a second wavelength region. In the example of FIG. 4, the interference signals are sampled eight times (that is, eight pieces of the A-scan information are acquired) while the wavelength of the light emitted from the light source 12 changes over one cycle, therefore the interference signals are acquired in each of the first to eighth wavelength regions within one cycle. Hereinbelow, only sampling in the first wavelength region and sampling in the second wavelength region will be explained in order to facilitate the explanation, however, samplings in the third to eighth wavelength regions are similarly performed. In this embodiment, the interference signals are sampled eight times while the wavelength of the light emitted from the light source 12 changes over one cycle, however, how many times the interference signals are sampled while the wavelength of the light changes over one cycle is not limited. It may be less than eight times, or may be more than eight times.

Figure 5A:
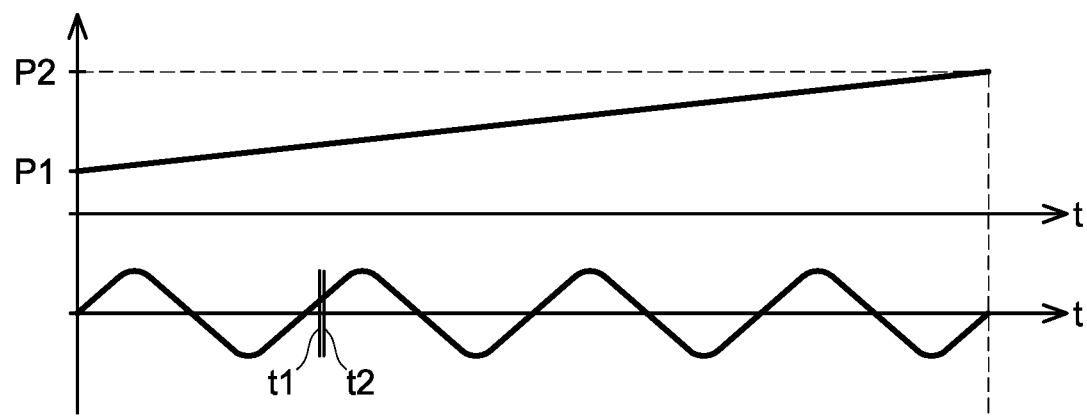
FIGS. 5A, 5B, and 5C are diagrams for explaining a relation between speed to change the wavelength of the light over one cycle and speed to change a scan angle, where
Figure 5B:
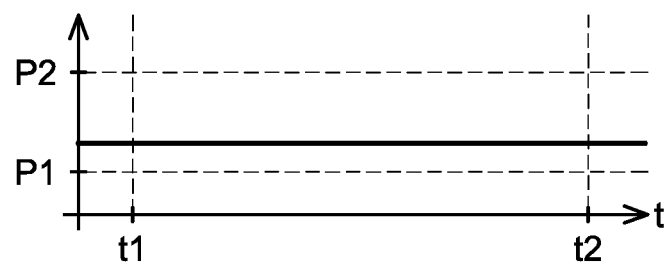

Further, in the present embodiment, a speed to change the scan angle is set to be sufficiently slow relative to a speed to sweep the light emitted from the light source 12 (which is a speed to change the wavelength of the light over one cycle). This allows acquisition of all the interference signals that constitute whole one piece of A-scan information successively. Hereinbelow, explanation continues with reference to FIGS. 5A and 5B. An upper part of FIG. 5A shows a relationship between irradiation positions of the measurement light and time in a case where a position of the subject eye 100 that is irradiated with the measurement light is scanned from position P1 to P2, and a lower part of FIG. 5A shows a relationship between the wavelength of the light emitted from the light source 12 and time. Further, FIG. 5B shows irradiation positions of the measurement light during a time period from time t1 to t2 in the sampling in the first wavelength region.

As shown in FIG. 5A, while a position of the subject eye 100 irradiated with the measurement light is scanned from position P1 to P2 (see the upper part of the drawing), the wavelength of the light emitted from the light source 12 changes over plural cycles (four cycles in FIG. 5A) (see the lower part of the drawing). As described above, in this embodiment, the sampling is performed plural times (such as eight times) while the wavelength of the light emitted from the light source 12 changes over one cycle, and one piece of A-scan information is acquired in each of the samplings. When the speed to change the scan angle is set to be sufficiently slow relative to the speed to change the wavelength of the light over one cycle, a position of the subject eye 100 irradiated with the light hardly changes during the time period from the time t1 to t2, which is required for one sampling, as shown in FIG. 5B. Thus, the interference signals on one scan line, that is, all the interference signals that constitute whole one piece of A-scan information, can be acquired within the time period from the time t1 to t2.

Figure 5C:
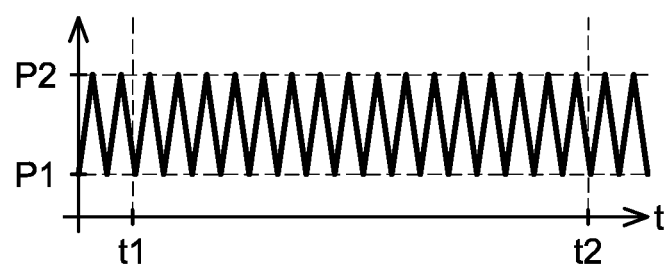

Aside from the method of the present embodiment, for example, considerations may be given to a method in which sampling is performed while a position of the subject eye 100 irradiated with the measurement light is scanned at a fast speed, as a method of acquiring plural pieces of A-scan information within a short period of time. FIG. 5C shows a relationship between irradiation positions of the measurement light and time in a case where the irradiation position is scanned at a fast speed, as a comparative example. As shown in FIG. 5C, in the method of the comparative example, the irradiation position of the measurement light reciprocates between the positions P1 and P2 plural times (about sixteen times in FIG. 5C) during the time period from the time t1 to t2 (that is, the time required for the sampling in the first wavelength region in the present embodiment). That is, the irradiation position is not constant and continues to change during the time period from the time t1 to t2. Due to this, all the interference signals constituting whole one piece of A-scan information cannot be acquired within the time period from time t1 to t2. With this method of comparative example, the interference signals are discretely acquired at different irradiation positions between the positions P1 and P2 during the time period from the time t1 to t2. Here, for example, it is assumed that n pieces of A-scan information are acquired. In this case, during the time period from the time t1 to t2, a part of the interference signals constituting the first piece of A-scan information, a part of the interference signals constituting the second piece of A-scan information, and a part of the interference signals constituting each of the remaining pieces of A-scan information up to the $n^{th}$ piece of A-scan information are acquired. As such, by discretely acquiring the interference signals at different irradiation positions similar to the above from time t2 and thereon, all the interference signals constituting the n pieces of A-scan information can be acquired. Thus, acquiring whole one piece of A-scan information by using the method of scanning the irradiation position at a fast speed requires the same amount of time that is required to acquire A-scan information on plural scan lines (n lines).

If the subject eye 100 moves, for example, by involuntary eye movements during acquisition of one piece of A-scan information, the position of the subject eye 100 thereby changes, which results in inaccurate measurement of the positional relationship between the interference signals included in the one piece of A-scan information. Therefore, the measurement must be performed with the subject eye 100 immovable while whole one piece of A-scan information is acquired. In the present embodiment, all the interference signals constituting whole one piece of A-scan information are acquired successively, thus the time required for acquiring one piece of A-scan information is short. As such, the subject eye 100 is less likely to move while one piece of A-scan information is acquired, thus an influence caused by the movements of the subject eye 100 can be mitigated.

The observation optical system 50 irradiates the subject eye 100 with observation light through the hot mirror 48 and captures reflected light that is reflected from the subject eye 100 (that is, reflected light of the observation light). Here, the hot mirror 48 reflects the light from the light source 12, while it allows light from a light source of the observation optical system 50 to pass therethrough. As a result, in the ophthalmic apparatus 1 of the present embodiment, it is possible to perform the measurement by the interference optical system 14 and the observation of the anterior part of the eye by the observation optical system 50 at the same time. An observation optical system used in a well-known ophthalmic apparatus can be used as the observation optical system 50. For this reason, detailed configuration thereof is not explained herein.

Further, the ophthalmic apparatus 1 of the present embodiment is provided with a position adjuster 16 (shown in FIG. 2) configured to adjust a position of the measurement unit 10 with respect to the subject eye 100, and a first driver 54 (shown in FIG. 2) configured to drive the position adjuster 16. The position of the measurement unit 10 with respect to the subject eye 100 is adjusted by driving the first driver 54.

Figure 2:
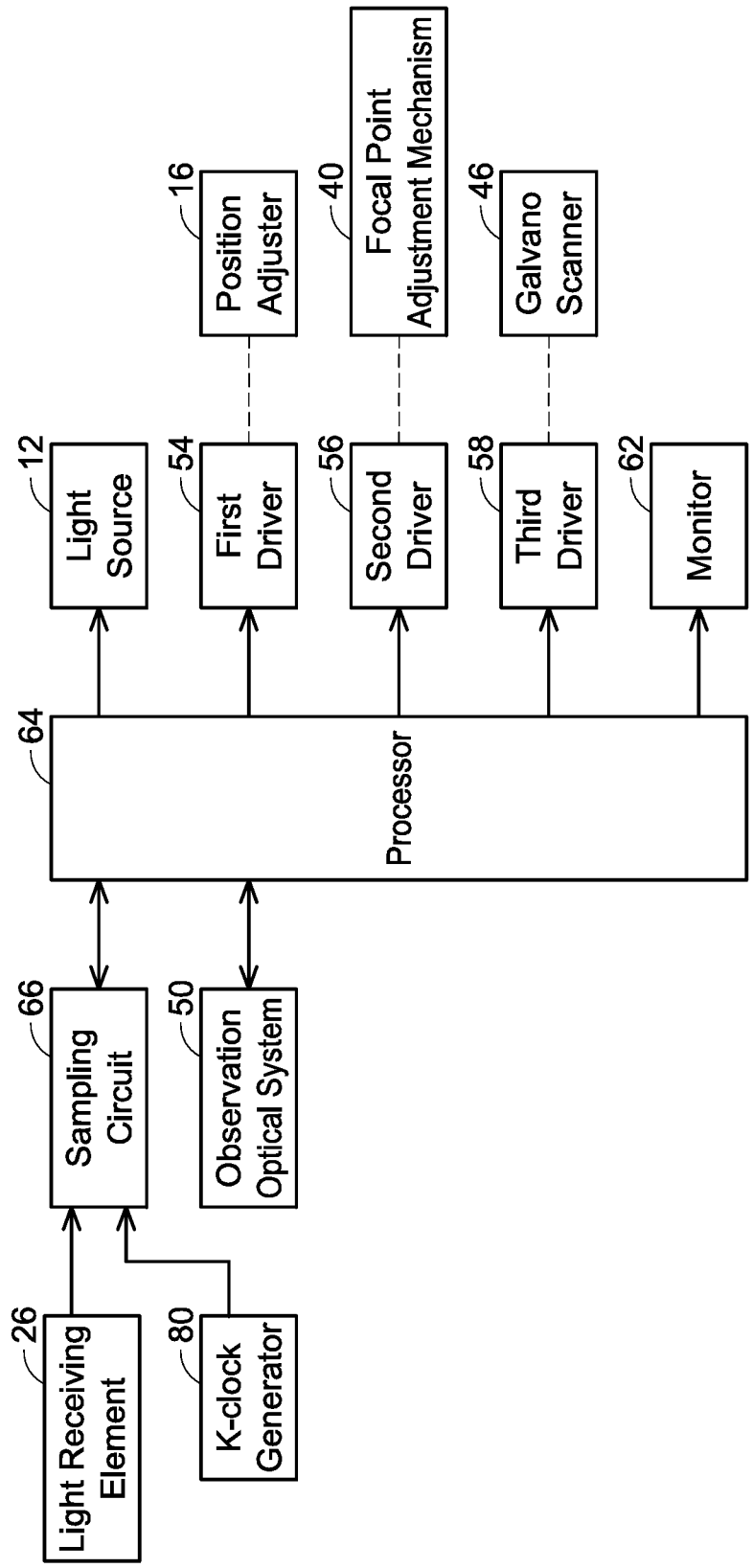
FIG. 2 is a block diagram of a control system of the ophthalmic apparatus according to the first embodiment.

Next, a configuration of a control system of the ophthalmic apparatus 1 according to the present embodiment will be described. As shown in FIG. 2, the ophthalmic apparatus 1 is controlled by the processor 64. The processor 64 includes a microcomputer (microprocessor) configured of CPU, ROM, RAM, and the like. The processor 64 is connected to the light source 12, the first to third drivers 54 to 58, a monitor 62, and the observation optical system 50. The processor 64 is configured to control on/off of the light source 12, and drive the position adjuster 16, the focal point adjustment mechanism 40, and the Galvano scanner 46 by controlling the first to third drivers 54 to 58. Further, the processor 64 is configured to control the observation optical system 50 to display an image of the anterior eye part captured by the observation optical system 50 on the monitor 62.

Figure 6:
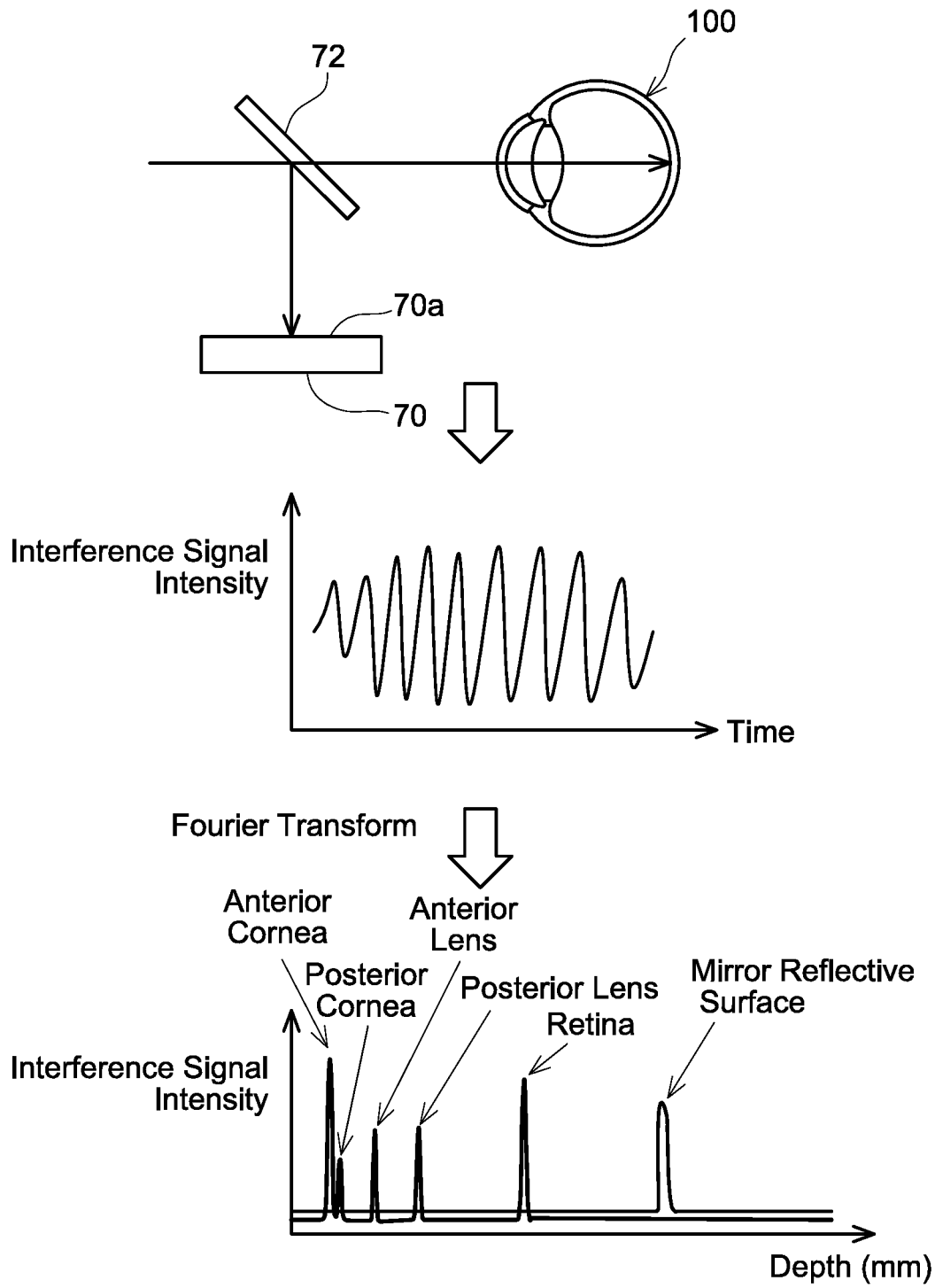
FIG. 6 shows diagrams for explaining a procedure to process an interference signal waveform.

Further, the processor 64 is connected to the sampling circuit 66. The processor 64 is configured to output a trigger signal for causing the sampling circuit 66 to start the sampling. Upon input of the trigger signal, the sampling circuit 66 acquires the interference signals at the timings defined by the K-clock signals over a preset time period. The interference signals sampled by the sampling circuit 66 are inputted to the processor 64. As described above, the interference signals outputted from the light receiving element 26 are signals of which intensities change over time as shown in FIG. 6, and these signals include signals of interference wave that includes combinations of the reference light and the reflected light reflected from respective parts of the subject eye 100 (anterior and posterior surfaces of the cornea 102, anterior and posterior surfaces of the crystalline lens 104, and a surface of the retina 106) and combination of the reference light and the reflected light reflected from the reflection surface 70a of the mirror 70. The processor 64 Fourier-transforms the sampled interference signals to separate, from the interference signals, interference signal components of the respective parts of the subject eye 100 (anterior and posterior surfaces of the cornea 102, anterior and posterior surfaces of the crystalline lens 104, and a surface of the retina 106) and the reflection surface 70a of the mirror 70 (see a lowermost graph of FIG. 6). Due to this, the processor 64 can specify positions of the respective parts of the subject eye 100 and a position of the reflection surface 70a of the mirror 70.

In the present embodiment, the processor 64 acquires the sampled interference signals (data) by dividing them in data units each constituting one piece of A-scan information, however, other configurations may be employed. For example, the processor 64 may acquire the sampled interference signals as one piece of continuous data that encompasses all of the plural pieces of A-scan information. In this case, the processor 64 may adapt window functions having different center positions to the acquired data to extract the individual pieces of A-scan information from the continuous data. The processor 64 can separate the interference signal components of the respective parts of the subject eye 100 and the reflection surface 70a of the mirror 70 for each A-scan information by Fourier-transforming each of the extracted individual pieces of A-scan information, and thus can specify the positions of the respective parts of the subject eye 100 and the position of the reflection surface 70a of the mirror 70.

Figure 9A:
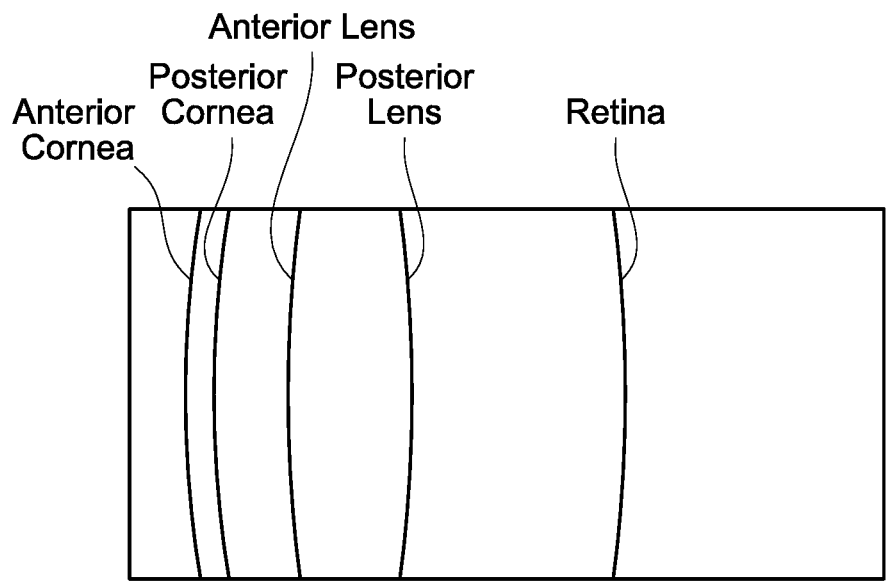
FIGS. 9A and 9B are schematic diagrams showing tomographic images generated by using acquired A-scan information, where
Figure 9B:
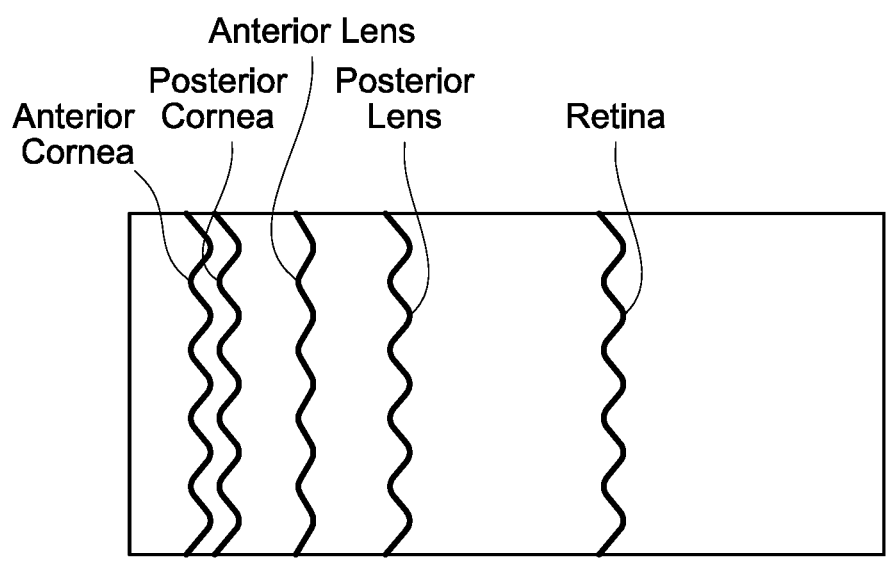

Next, a process of correcting distortion of the interference signals, which is caused by the samplings of the interference signals in the different frequency bands, using the ophthalmic apparatus 1 of the present embodiment will be described with reference to FIG. 7. As described above, in the present embodiment, the A-scan information is acquired plural times (such as eight times) in the different frequency bands each time the light outputted from the light source 12 changes over one cycle. However, acquiring the A-scan information in each of the different frequency bands may result in differences in signal intensities and positions of the interference signals detected for the A-scan information. If a tomographic image is generated using such data that have differences in signal intensities and positions, distortion (see FIG. 9B) and/or contrast inconsistency may be seen in the generated tomographic image, as a result of which a condition of the subject eye 100 cannot accurately be identified. The ophthalmic apparatus 1 of the present embodiment is configured to correct such signal intensity differences and positional differences of the interference signals caused by the interference signals being sampled in the different frequency bands.

Figure 7:
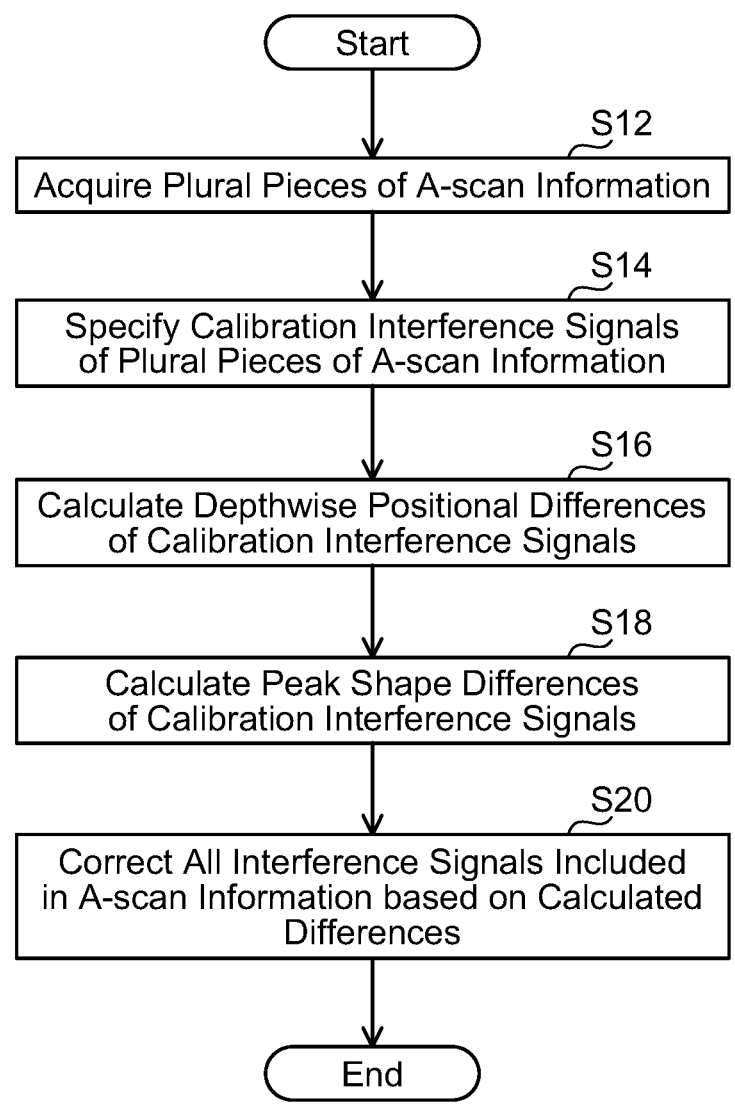
FIG. 7 is a flowchart showing an example of a process of correcting distortion of interference signals caused in samplings of the interference signals in different frequency bands.

As shown in FIG. 7, firstly, the processor 64 acquires plural pieces of A-scan information sampled in different wavelength regions (that is, different frequency bands) (S12). The plural pieces of A-scan information are acquired by the following procedure. Firstly, an examiner operates an operation member, such as a joystick, which is not shown, to position the measurement unit 10 relative to the subject eye 100. That is, the processor 64 drives the position adjuster 16 by the first driver 54 according to the operation of the examiner on the operation member. Due to this, positions of the measurement unit 10 relative to the subject eye 100 in xy directions (vertical and horizontal directions) and a position thereof relative to the subject eye 100 in a z direction (direction along which the measurement unit 10 progresses and retracts) are adjusted. Further, the processor 64 drives the second driver 56 to adjust the focal point adjustment mechanism 40. Due to this, a focal point position of the light from the light source 12 with which the subject eye 100 is irradiated comes to be located at a predetermined position on the subject eye 100 (such as on the anterior surface of the cornea 102).

Then, the interference signals are sampled in a specific wavelength region. Here, on the assumption that the specific wavelength region in which the interference signals are sampled first is the first wavelength region, a procedure of sampling the interference signals in the specific wavelength region (first wavelength region) will be described. Firstly, in order to generate a trigger signal, the processor 64 detects a specific wavelength within the first wavelength region. A method of detecting the specific wavelength is not particularly limited, and the specific wavelength may be detected by using an FBG (fiber bragg gratings) or an etalon, for example. The processor 64 generates the trigger signal for stating the sampling in the first wavelength region, based on the detected wavelength. For example, the processor 64 detects a wavelength that corresponds to time t1 in FIG. 4, which is a start timing of the sampling in the first wavelength region, by using the FBG and generates the trigger signal based on the detected wavelength. By doing so, the processor 64 can generate the trigger signal set to the start timing of the sampling in the first wavelength region (that is, time t1). In this embodiment, a specific wavelength (such as the wavelength corresponding to time t1) within a specific wavelength region (such as the first wavelength region) is detected to generate a trigger signal for starting the sampling in the specific wavelength region, however, other configurations may be employed. For example, in order to generate a trigger signal for starting the sampling in a specific wavelength region (such as the first wavelength region), a specific wavelength outside the specific wavelength region (such as the first wavelength region) may be detected. That is, the specific wavelength outside the specific wavelength region (such as the first wavelength region) may be detected to generate a trigger signal for starting the sampling when a predetermined time period has elapsed since the specific wavelength was detected (at time t1, for example).

The processor 64 outputs the generated trigger signal to the sampling circuit 66. When the trigger signal is inputted to the sampling circuit 66 from the processor 64 in a state where the interference signals and the K-clock signals are inputted to the sampling circuit 66, the sampling circuit 66 acquires the interference signals at the timings defined by the K-clock signals. This acquisition of the interference signals is performed over a preset time period (such as the time period from t1 to t2). Due to this, the interference signals (one piece of A-scan information) in the first wavelength region are acquired. These acquired interference signals include the measurement interference signal and the calibration interference signal. The acquired interference signals are inputted to the processor 64 from the sampling circuit 66.

When the sampling of the interference signals in the first wavelength region is completed, the sampling of the interference signals is performed in the subsequent wavelength region (that is, the second wavelength region). The sampling circuit 66 acquires the interference signals according to the K-clock signals when the wavelength of the light emitted from the light source 12 becomes a wavelength corresponding to the start of the second wavelength region. Specifically, based on the trigger signal, the sampling circuit 66 starts the sampling at time t3 when a predetermined time has elapsed since the time t1 which is a start timing of the sampling in the first wavelength region. As above, the sampling circuit 66 can start the sampling at the time t3 which is a start timing of the sampling in the second wavelength region. The acquisition of the interference signals is performed over a preset time period (time period from t3 to t4). These acquired interference signals include the measurement interference signal and the calibration interference signal. The acquired interference signals are inputted to the processor 64 from the sampling circuit 66. The sampling in the second wavelength region may be started based on a trigger signal for starting the sampling in the second wavelength region. Specifically, the trigger signal for starting the sampling in the second wavelength region may be generated to define the start timing of the sampling in the second wavelength region based on the detected specific wavelength (wavelength corresponding to the time t1 in FIG. 4). That is, the processor 64 may generate the trigger signal such that the sampling is started at the time t3 when a predetermined time period has elapsed since the time t1 corresponding to the detected specific wavelength. Further, the trigger signal for starting the sampling in the second wavelength region may be generated by detecting a wavelength corresponding to the time t3 which is the timing to start the sampling in the second wavelength region. The above-described processes are performed for each scan line in each of the wavelength regions. As a result, the plural pieces of A-scan information sampled in the different wavelength regions are acquired.

In the present embodiment, the wavelength regions in which the interference signals are sampled are independent from each other without overlapping each other (see FIG. 4), however, the wavelength regions in which the interference signals are sampled may partially overlap with each other. For example, as shown in FIG. 8, the light emitted from the light source 12 may be in the first wavelength region from time t5 to t7 and in the second wavelength region from time t6 to t8, which means the first wavelength region and the second wavelength region may overlap with each other from time t6 to t7. In such a case, the interference signals are successively sampled in the plurality of wavelength regions that overlap with each other (such as, in the first to fourth wavelength regions in FIG. 8) and are stored in a memory (not shown) of the processor 64. Then, data corresponding to each of the wavelength regions is extracted from the sampled data. Due to this, even in a case where the wavelength regions in which the interference signals are sampled partially overlap with each other, the positions of the respective parts of the subject eye 100 and the position of the reflection surface 70a of the mirror 70 can suitably be specified in each of the wavelength regions.

When the plural pieces of A-scan information are acquired in step S12, the processor 64 specifies a waveform of the calibration interference signal (more specifically, a signal waveform obtained after the Fourier transform, such as a point spread function signal waveform) for each of the plural pieces of A-scan information (S14). As described above, the optical path length L1 from the zero point of the calibration optical system is set to be longer than the distance from the zero point to the retina 106 of the subject eye 100 (see FIG. 3). Due to this, the position of the reflection surface 70a is detected outside the measurement region of the subject eye 100 (more specifically, detected at a position deeper than the measurement region). Due to this, by Fourier-transforming the interference signals including the measurement interference signal and the calibration interference signal, the calibration interference signal can be specified from among the interference signals.

Next, the processor 64 calculates differences in depthwise positions of the waveforms of the calibration interference signals specified in step S14 (S16) between the plural pieces of the A-scan information. Sampling the interference signals in the different frequency bands results in different depthwise positions of the waveforms of the interference signals among the frequency bands. Such positional differences are caused, for example, in a case where the measurement optical system, the reference optical system, and the calibration optical system use fibers, due to differences between a length of the fiber of the measurement optical system (or the calibration optical system) and a length of the fiber of the reference optical system, and in this case, the depthwise positions of the waveforms of the interference signals shift. Further, the positional differences may also be caused due to a change in resolution caused by wavelength dispersion in the K-clock generator 80. The depthwise positional differences of the waveforms of the interference signals depend on characteristics of individual ophthalmic apparatuses 1 and characteristics of individual light sources 12, thus what sort of positional differences is to be caused (such as, whether the positions are shifted or the positions are different due to change in the resolution) can be identified in advance. If a tomographic image is generated using data that have depthwise differences in the waveforms of the interference signals, distortion is seen in the generated tomographic image (see FIG. 9) because depthwise measurement values differ between the A-scan information, despite the image indicating the same target. In view of this, differences in the depthwise positions of the waveforms of the detected interference signals between the respective A-scan information are calculated.

The calibration interference signal is a signal of interference wave which is combination of the reflected light reflected from the reflection surface 70a of the mirror 70 and the reference light, and the optical path length of the calibration light is constant and does not change. As such, the calibration interference signals included in the plural pieces of A-scan information all indicate the same target (that is, the reflection surface 70a of the mirror 70), and all of them are supposed to be detected at the same depthwise position. By calculating differences in the depthwise positions of the waveforms of the calibration interference signals between the plural pieces of A-scan information, which are supposed to be detected at the same depth position, differences in the depthwise positions of all the interference signals (that is, the calibration interference signals and the measurement interference signals) that are caused by the samplings in the different frequency bands can be calculated. For example, the processor 64 calculates a difference between a depthwise position of the waveform of the calibration interference signal included in the A-scan information sampled in the first wavelength region (hereinbelow may be termed a first calibration waveform) and a depthwise position of the waveform of the calibration interference signal included in the A-scan information sampled in the second wavelength region (hereinbelow may be termed a second calibration waveform). This difference can be said to be a depthwise positional difference between all the interference signals sampled in the first wavelength region and all the interference signals sampled in the second wavelength region. Similarly, depthwise positional differences between the waveforms of the calibration interference signals of the respective A-scan information are calculated.

Next, the processor 64 calculates differences in shapes of the waveforms of the calibration interference signals specified in step S14 (hereinbelow may be termed peak shapes) between the plural pieces of A-scan information (S18). Sampling the interference signals in the different frequency bands results in different peak shapes of the waveforms of the interference signals detected in the respective frequency bands. If a tomographic image is generated by using such data having differences in the peak shapes of the waveforms of the interference signals, contrast inconsistency is seen in the generated tomographic image because the signal intensities differ between the plural pieces of A-scan information, despite the image indicating the same target. In view of this, differences in the peak shapes of the waveforms of the detected calibration interference signals between the respective A-scan information are calculated. For example, the processor 64 calculates a difference between a peak shape of the first calibration waveform and a peak shape of the second calibration waveform (such as a difference in heights, widths, or inclinations of the peak shapes). This difference can be said to be a signal intensity difference between all the interference signals sampled in the first wavelength region and all the interference signals sampled in the second wavelength region. Similarly, differences in the peak shapes of the waveforms of the calibration interference signals between the respective A-scan information are calculated.

Next, the processor 64 corrects all the interference signals in each A-scan information (that is, the calibration interference signal and the measurement interference signal) based on the differences calculated in step S16 and step S18 (S20). One piece of A-scan information includes the measurement interference signal specifying the respective parts of the subject eye 100 and the calibration interference signal specifying the mirror 70. The depthwise positional difference and the peak shape difference of the interference signals caused by the samplings in the different frequency bands occur in all the interference signals included in one piece of A-scan information similarly. That is, if the calibration interference signal in one piece of A-scan information has a difference, the measurement interference signal included in the same piece of A-scan information has the same difference. As such, a group of the measurement interference signal and the calibration interference signal included in the same piece of A-scan information is corrected by the differences calculated in step S16 and step S18.

For example, in a case where the depthwise positions of the interference signals simply shift between the A-scan information, the correction is performed as follows. Here, it is assumed that the calculation in step S16 finds that the depthwise position of the second calibration waveform is shifted by $+\Delta Z1$ relative to the depthwise position of the first calibration waveform. In this case, the processor 64 shifts the group of the interference signals (that is, the measurement interference signal and the calibration interference signal) included in the A-scan information sampled in the second wavelength region by $-\Delta Z1$. By this correction, the depthwise positions of the waveforms of the two calibration interference signals (that is, depthwise positions of the first calibration waveform and the second calibration waveform), which are supposed to be detected at the same depthwise position, are substantially matched to each other. As a result, the position of the measurement interference signal, which has the same difference as the calibration interference signal included in the A-scan information sampled in the second wavelength region, can also be corrected to a position that is free of the difference relative to the A-scan information sampled in the first wavelength region. In the present embodiment, the group of the interference signals included in the A-scan information sampled in the second wavelength region is shifted so that the depthwise positions of the first calibration waveform and the second calibration waveform substantially match each other, however, other configurations may be employed. In order to substantially match the depthwise positions of the first calibration waveform and the second calibration waveform each other, the group of the interference signals included in the A-scan information sampled in the first wavelength region may be shifted, or both the group of the interference signals included in the A-scan information sampled in the first wavelength region and the group of the interference signals included in the A-scan information sampled in the second wavelength region may be shifted.

Further, in a case where the depthwise positions of the interference signals are different between the A-scan information due to the change in the resolution, the correction is performed as follows. Here, it is assumed that, the depthwise position of the first calibration waveform is a distance Z1 apart from a certain reference position (such as the zero point) and the depthwise position of the second calibration waveform is a distance Z2 apart from the certain reference position. In this case, the processor 64 moves the group of the interference signals (that is, the measurement interference signal and the calibration interference signal) included in the A-scan information sampled in the second wavelength region by Z1/Z2 from the reference position. By this correction, the position of the first calibration waveform and the position of the second calibration waveform match each other, and further the positions of all the interference signals included in the A-scan information sampled in the second wavelength region are changed at the same rate. Due to this, even in the case where the positional difference is caused due to the change in the resolution, the A-scan information sampled in the second wavelength region can be corrected to the position free of the difference relative to the A-scan information sampled in the first wavelength region. In order to substantially match the depthwise positions of the first calibration waveform and the second calibration waveform each other, the group of the interference signals included in the A-scan information sampled in the first wavelength region may be moved, or both the group of the interference signals included in the A-scan information sampled in the first wavelength region and the group of the interference signals included in the A-scan information sampled in the second wavelength region may be moved.

In the above examples, the correction for the case where the depthwise positions of the interference signals simply shift between the A-scan information (shift correction) and the correction for the case where the depthwise positions of the interference signals are different between the A-scan information due to the change in the resolution (correction for resolution change) are described, however, other configurations may be employed. For example, in a case where the depthwise positions of the interference signals shift as well as are different due to the resolution change between the A-scan information, the depthwise positions of the interference signals (the measurement interference signal and the calibration interference signal) may be corrected by combining the shift correction and the correction for resolution change.

Similar to the above, the group of the interference signals included in each A-scan information is corrected so that the depthwise positions of the waveforms of all the calibration interference signals included in the plural pieces of A-scan information match each other. By generating a tomographic image by using the A-scan information corrected as above, distortion can be suppressed in the tomographic image.

Further, as for the differences in the waveform shapes of the interference signals between the plurali pieces of A-scan information as well, the group of the interference signals included in each A-scan information is corrected so that the peak shapes of the waveforms of the calibration interference signals included in the plural pieces of A-scan information match each other. Here, it is assumed that the height of the peak shape of the second calibration waveform is calculated as about 50% of the height of the peak shape of the first calibration waveform in step S18, for example. In this case, the signal intensities of the group of the interference signals (that is, the measurement interference signal and the calibration interference signal) included in the A-scan information sampled in the first wavelength region are changed to 50% so that the height of the peak shape of the first calibration waveform and the height of the peak shape of the second calibration waveform match each other. In order to match the height of the peak shape of the first calibration waveform and the height of the peak shape of the second calibration waveform each other, the signal intensities of the interference signals included in the A-scan information sampled in the second wavelength region may be increased, or both the signal intensities of the interference signals included in the A-scan information sampled in the first wavelength region and the signal intensities of the interference signals included in the A-scan information sampled in the second wavelength region may be changed.

Further, in a case where the widths of the peak shapes of the waveforms of the calibration interference signals differ between the plural pieces of A-scan information, for example, a width at a half the height of the peak shape of the waveform of the calibration interference signal included in each A-scan information (a so-called half-value width) is detected, and then the group of the interference signals included in each A-scan information prior to the Fourier transform is corrected so that the detected half-value widths match each other. After this, the corrected interference signals are Fourier-transformed. By doing so, the widths of the peak shapes of the waveforms of the interference signals are corrected. That is, for each of the A-scan information, the interference signals configuring each peak shape included in this A-scan information are corrected. Here, it is assumed that the half-value width of the peak shape of the Fourier-transformed second calibration waveform is calculated as about 50% of the half-value width of the peak shape of the Fourier-transformed first calibration waveform in step S18. In this case, spectrum shaping is performed on all the interference signals (that is, the measurement interference signal and the calibration interference signal) included in the A-scan information sampled in the first wavelength region before the interference signals are Fourier-transformed so that the half-value width of the peak shape of the Fourier-transformed first calibration waveform and the half-value width of the peak shape of the Fourier-transformed second calibration waveform match each other. After this, the interference signals to which the spectrum shaping has been performed are Fourier-transformed. By doing so, the A-scan information in which the widths of the peak shapes of the waveforms of the interference signals have been changed to 50% are obtained. A method of correcting the widths of the peak shapes of the waveforms of the interference signals is not limited to the one described above. For example, instead of the spectrum shaping, a window function may be applied to correct the widths of the peak shapes of the waveforms of the interference signals. By generating a tomographic image using the A-scan information corrected as above, contrast inconsistency in the tomographic image can be suppressed. Further, depthwise dimensions of the respective intraocular parts are displayed at the same sizes, and thus sharpness of the tomographic image is improved.

In the present embodiment, the light reflected on the reflection surface 70a of the mirror 70 is used as the calibration light, however, the calibration light is not limitated so. Any reflected light may be used as calibration light as long as it has a known optical path length in an ophthalmic apparatus, and for example, reflected light on the reflection surface of the optical member (such as the convex lens 42) provided in the measurement optical system may be used as the calibration light. By generating the calibration light using the optical member provided in the measurement optical system, the calibration light can be generated without increase in the number of components.

Second Embodiment

In the first embodiment above, the mirror 70 for generating the calibration light is provided at a position that is not on the optical path of the measurement optical system inside the ophthalmic apparatus 1, however, the position is not limited so. For example, a mirror 170 for generating calibration light may be disposed at a position that is on an optical path of a measurement optical system external to an ophthalmic apparatus 2. The ophthalmic apparatus 2 of the present embodiment differs from the ophthalmic apparatus 1 of the first embedment in regard to an optical path of calibration optical system, and is substantially the same as the ophthalmic apparatus 1 regarding other configurations. Thus, descriptions on the same configurations as those of the first embodiment will be omitted.

Figure 10:
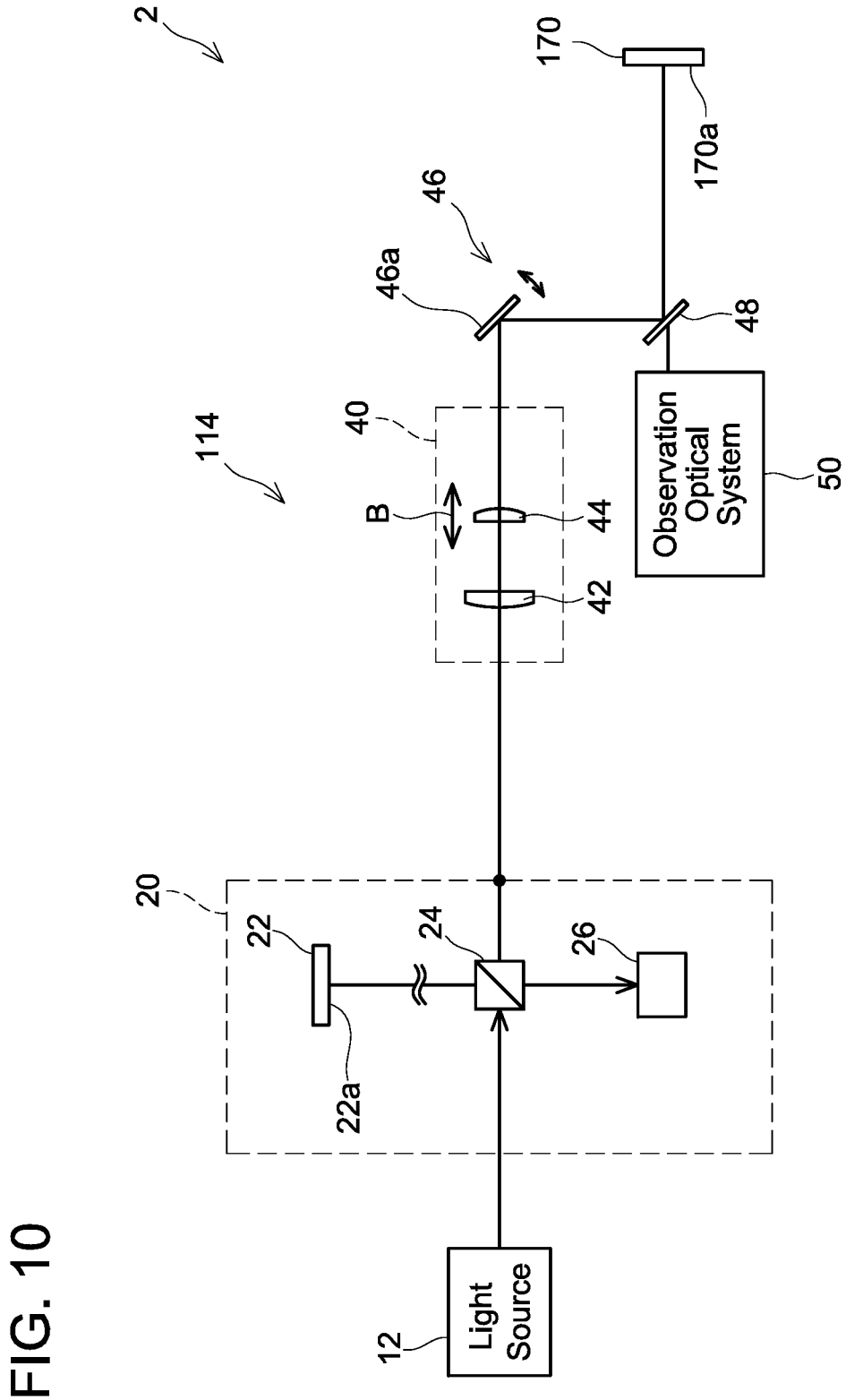
FIG. 10 shows a schematic configuration of an optical system of an ophthalmic apparatus according to a second embodiment.

As shown in FIG. 10, the ophthalmic apparatus 2 includes an interference optical system 114. The interference optical system 114 is configured of the light source 12, the measurement optical system, the reference optical system, a calibration optical system, and the light receiving element 26. This calibration optical system is configured of the beam splitter 24, the focal point adjustment mechanism 40, the Galvano scanner 46, the hot mirror 48, and the mirror 170. Light emitted from the light source 12 reaches a reflection surface 170a of the mirror 170 through the beam splitter 24, the focal point adjustment mechanism 40, the Galvano scanner 46, and the hot mirror 48. Light reflected on the mirror 170 is guided to the light receiving element 26 through the hot mirror 48, the Galvano scanner 46, the focal point adjustment mechanism 40, and the beam splitter 24.

In this embodiment, an optical path of the calibration optical system substantially matches an optical path of the measurement optical system, and the mirror 170 is disposed on the optical path of the measurement optical system external to the ophthalmic apparatus 2 in a state of being attached to an attachment (not shown). When the mirror 170 is attached to the attachment, the mirror 170 is disposed on the optical path of the calibration optical system and thus the subject eye 100 cannot be disposed on the optical path of the measurement optical system. Therefore, when the mirror 170 is attached to the attachment, the light receiving element 26 receives the reflected light from the reflection surface 170a of the mirror 170 (that is, calibration light). On the other hand, when the mirror 170 is not attached to the attachment, the subject eye 100 can be disposed on the optical path of the measurement optical system. Therefore, the light receiving element 26 receives reflected light from the subject eye 100 (that is, measurement light) when the mirror 170 is not attached to the attachment and the subject eye 100 is disposed on the optical path of the measurement optical system. That is, in the ophthalmic apparatus 2 of the present embodiment, the calibration light and the measurement light are not simultaneously generated, and the calibration light and the measurement light are generated at different timings. The mirror 170 is an example of a "calibration member".

In the present embodiment, firstly the processor 64 acquires plural pieces of A-scan information sampled in different wavelength regions (that is, frequency bands) in a state where the mirror 170 is attached to the attachment. The plural pieces of A-scan information acquired here include only calibration interference signals, and do not include measurement interference signals. Then, the processor 64 specifies a waveform of the calibration interference signal for each A-scan information, and calculates depthwise positional differences and peak shape differences between the waveforms of the calibration interference signals. These processes are substantially similar to the processes of steps S12 to S18 of the first embodiment, thus detailed descriptions thereof will be omitted. The depthwise positional differences and the peak shape differences between the waveforms of the calibration interference signals of the A-scan information are stored in a memory (not shown) of the processor 64. The mirror 170 is detached from the attachment after the plural pieces of A-scan information including the calibration interference signals are acquired.

When the mirror 170 is not attached to the attachment, the subject eye 100 can be measured using the ophthalmic apparatus 2 (that is, plural pieces of A-scan information can be acquired for the subject eye 100). Since this process of acquiring plural pieces of A-scan information for the subject eye 100 is substantially similar to the process of step S12 of the first embodiment, thus detailed descriptions thereof will be omitted. The plural pieces of A-scan information acquired here include only the measurement interference signals and do not include the calibration interference signals. Then, the processor 64 corrects the measurement interference signals based on the depthwise positional differences and the peak shape differences between the waveforms of the calibration interference signals of the A-scan information which are stored in the memory. Since this process is substantially similar to the process of step S20 of the first embodiment, thus detailed descriptions thereof will be omitted. As above, even in a case where the measurement interference signals and the calibration interference signals are acquired at different timings, the signal intensity differences and positional differences of the interference signals caused by the samplings having been performed in the different frequency bands can suitably be corrected.

Specific examples of the disclosure herein have been described in detail, however, these are mere exemplary indications and thus do not limit the scope of the claims. The art described in the claims includes modifications and variations of the specific examples presented above. Technical features described in the description and the drawings may technically be useful alone or in various combinations, and are not limited to the combinations as originally claimed.

What is claimed is:

1. An ophthalmic apparatus configured to measure a subject eye by using an optical interferometry, the ophthalmic apparatus comprising:
   a light source of wavelength sweeping type;
   a reference optical system configured to guide light from the light source so as to acquire reference light from the light from the light source;
   a calibration optical system configured to guide the light from the light source so as to acquire calibration light from the light from the light source;

a light receiving element configured to receive calibration interference light, the calibration interference light being a combination of the calibration light and the reference light;
a signal processor configured to sample a calibration interference signal, the calibration interference signal being outputted from the light receiving element when the light receiving element receives the calibration interference light;
a processor; and
a memory storing computer-readable instructions therein, wherein
a frequency of the light from the light source changes cyclically,
the signal processor is configured to sample the calibration interference signal in at least a first frequency band and a second frequency band within an entire frequency band that corresponds to one cycle of change in the frequency of the light from the light source, the second frequency band being different from the first frequency band, the first frequency band being used for measuring a specific region of the subject eye, and the second frequency band being used for measuring the specific region of the subject eye, and
the computer-readable instructions, when executed by the processor, cause the ophthalmic apparatus to calculate a difference between a first waveform and a second waveform, the first waveform being a waveform of the calibration interference signal that is sampled in the first frequency band and Fourier transformed, the second waveform being a waveform of the calibration interference signal that is sampled in the second frequency band and Fourier transformed.

2. The ophthalmic apparatus according to claim 1, wherein
the computer-readable instructions, when executed by the processor, cause the ophthalmic apparatus to calculate a difference between a position of the first waveform and a position of the second waveform in a depth direction.

3. The ophthalmic apparatus according to claim 1, wherein
the computer-readable instructions, when executed by the processor, cause the ophthalmic apparatus to calculate a difference between a shape of the first waveform and a shape of the second waveform.

4. The ophthalmic apparatus according to claim 1, further comprising a measurement optical system configured to irradiate the subject eye with the light from the light source and to guide reflected light from the subject eye,
wherein
the calibration optical system comprises a calibration member comprising a reflection surface configured to reflect the light from the light source,
the calibration member is detachably disposed on an optical path of the measurement optical system, and
when the calibration member is not disposed on the optical path of the measurement optical system, the optical path of the measurement optical system is capable of having the subject eye disposed thereon.

5. The ophthalmic apparatus according to claim 1, further comprising a measurement optical system configured to irradiate the subject eye with the light from the light source and to guide reflected light from the subject eye,
wherein
the calibration optical system comprises a calibration member comprising a reflection surface configured to reflect the light from the light source,
at least a part of an optical path of the calibration optical system is configured not to overlap with an optical path of the measurement optical system, and
the calibration member is not disposed on the optical path of the measurement optical system and is disposed on the optical path of the calibration optical system.

6. The ophthalmic apparatus according to claim 1, further comprising a measurement optical system configured to irradiate the subject eye with the light from the light source and to guide reflected light from the subject eye,
wherein
an optical path of the calibration optical system is configured to overlap with a part of an optical path of the measurement optical system, and
the calibration light is generated from reflected light from a reflection surface of an optical member which the measurement optical system comprises.

7. The ophthalmic apparatus according to claim 1, further comprising a measurement optical system configured to irradiate the subject eye with the light from the light source and to guide reflected light from the subject eye,
wherein
the light receiving element is further configured to receive measurement interference light, the measurement interference light being a combination of the reflected light from the subject eye and the reference light,
the signal processor is further configured to sample a measurement interference signal, the measurement interference signal being outputted from the light receiving element when the light receiving element receives the measurement interference light, and
the computer-readable instructions, when executed by the processor, cause the ophthalmic apparatus to correct, based on the calculated difference, at least one of the measurement interference signal that is sampled and the measurement interference signal that is sampled and Fourier transformed.

* * * * *